(12) United States Patent
Breuil et al.

(10) Patent No.: US 9,545,623 B2
(45) Date of Patent: Jan. 17, 2017

(54) NICKEL-BASED CATALYTIC COMPOSITION AND METHOD OF OLIGOMERIZATION OF OLEFINS USING SAID COMPOSITION

(75) Inventors: Pierre-Alain Breuil, Lyon (FR); Adrien Boudier, Lyon (FR); Lionel Magna, Lyon (FR); Helene Olivier-Bourbigou, Saint Genis-Laval (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 706 days.

(21) Appl. No.: 13/604,038

(22) Filed: Sep. 5, 2012

(65) Prior Publication Data

US 2013/0066128 A1 Mar. 14, 2013

(30) Foreign Application Priority Data

Sep. 8, 2011 (FR) ...................... 11 02731

(51) Int. Cl.
| | | |
|---|---|---|
| *B01J 21/00* | (2006.01) | |
| *B01J 23/00* | (2006.01) | |
| *B01J 25/00* | (2006.01) | |
| *B01J 29/00* | (2006.01) | |
| *B01J 31/00* | (2006.01) | |
| *B01J 31/18* | (2006.01) | |
| *C07C 2/32* | (2006.01) | |
| *C07C 2/34* | (2006.01) | |

(52) U.S. Cl.
CPC .............. *B01J 31/1815* (2013.01); *C07C 2/32* (2013.01); *C07C 2/34* (2013.01); *B01J 2231/12* (2013.01); *B01J 2531/847* (2013.01); *C07C 2531/18* (2013.01); *C07C 2531/22* (2013.01); *Y02P 20/52* (2015.11)

(58) Field of Classification Search
USPC ....................................... 502/150, 100, 164
See application file for complete search history.

(56) References Cited

U.S. PATENT DOCUMENTS

| 7,229,943 B2 * | 6/2007 | Gibson | ................ C08F 4/7006 502/103 |
|---|---|---|---|
| 2006/0094588 A1 * | 5/2006 | Gibson | ................ C08F 4/7006 502/103 |
| 2013/0066128 A1 * | 3/2013 | Breuil | ................ B01J 31/1815 585/511 |

FOREIGN PATENT DOCUMENTS

WO 02/38625 A1 5/2002

OTHER PUBLICATIONS

Wu, A. et al., Database CA [Online] Chemical Abstract Service, Columbus, Ohio, US; 2010, "Antimicrobial activities and synthesis of four new complexes with Schiff base condensed by 1-methyl-2-imidazolecarboxaldehyde and 2-aminoethanol," XP002671896, Database accession No. 2010:1425762; Search Report, dated Mar. 21, 2012, issued in corresponding FR11/02.731.
Popescu, A. et al., Database CA [Online] Chemical Abstract Service, Columbus, Ohio, US; 2000, "Carbonic anhydrase inhibitors. Part 67. Schiff bases of some aromatic sulfonamides and their metal complexes: towards more selective inhibitors of carbonic anhydrase isozyme IV," XP002671897, Database accession No. 2000:836053; Search Report, dated Mar. 21, 2012, issued in corresponding FR11/02.731.
He, Hongshan et al. "Structural and Spectroscopic Study of Reactions between Chelating Zinc-Binding Groups and Mimics of the Matrix Metalloproteinase and Disintegrin Metalloprotease Catalytic Sites: The Coordination Chemistry of Metalloprotease Inhibition," Inorganic Chemistry, Oct. 1, 2005, vol. 44 No. 21, pp. 7431-7442; Search Report, dated Mar. 21, 2012, issued in corresponding FR11/02.731.
Search Report and Written Opinion, dated Mar. 21, 2012, issued in corresponding FR11/02.731.

* cited by examiner

*Primary Examiner* — James McDonough
(74) *Attorney, Agent, or Firm* — Millen, White, Zelano and Branigan, P.C.

(57) ABSTRACT

The present invention describes a novel catalytic composition comprising at least one nickel complex, said complex being obtained from a mixture comprising at least one nickel precursor A with at least one imino-imidazole ligand B and a method of oligomerization of olefins using said catalytic composition.

14 Claims, No Drawings

NICKEL-BASED CATALYTIC COMPOSITION AND METHOD OF OLIGOMERIZATION OF OLEFINS USING SAID COMPOSITION

The present invention relates to the oligomerization of olefins comprising from 2 to 10 carbon atoms and in particular the dimerization of ethylene. A subject of the invention is to provide a novel nickel-based catalytic composition and a method of oligomerization of olefins using said particular catalytic composition.

PRIOR ART

It is known to prepare catalytic compositions for dimerization or codimerization of monoolefins such as ethylene, propylene, butenes or pentenes. Among these catalysts, the products obtained by reaction of π-allyl nickel phosphine halides with Lewis acids, as described in French patent FR-B-1 410 430, the products obtained by reaction of nickel phosphine halides with Lewis acids, as described in patent U.S. Pat. No. 3,485,881, and the products obtained by reacting certain nickel carboxylates with hydrocarbylaluminium halides, as described in patent U.S. Pat. No. 3,321,546 may in particular be mentioned.

Nearly all these catalytic compositions utilize a ligand that is an organic compound of phosphorus. These systems are known to be selective for the dimerization of ethylene, as described in patent U.S. Pat. No. 3,485,881. However, it is preferable to be able to have phosphorus-free oligomerization catalysts. One possibility would be to use catalysts in which nickel is deposited on a mineral support comprising acidic sites, such as silica, alumina or silica-aluminas. However, these are solid catalysts, in contrast to the liquid-phase catalytic compositions of the invention.

The use of catalytic compositions comprising a precursor of nickel, of chromium or of vanadium and at least one ligand of the imino-imidazole type, functionalized or not, and preferably of the functionalized imino-benzimidazole type, permitting the oligomerization and the (co)polymerization of ethylene with or without another olefin, was described recently, in patent applications WO 2004/083263 and WO 2005/111099.

One objective of the invention is to provide a novel catalytic composition for the oligomerization of olefins comprising from 2 to 10 carbon atoms and in particular the dimerization of ethylene.

Another objective of the invention is to provide a method of oligomerization of olefins comprising from 2 to 10 carbon atoms and in particular a method of dimerization of ethylene, utilizing said catalytic composition, said method having improved catalytic activity.

It has now been found, unexpectedly, that a novel catalytic composition obtained by mixing at least one nickel precursor, at least one functionalized or unfunctionalized imino-imidazole ligand, optionally in combination with an activating agent, in the presence or absence of a solvent, has improved activity for the oligomerization of olefins having from 2 to 10 carbon atoms, in particular the dimerization of olefins, and even more particularly very high selectivity for the dimerization of ethylene.

DETAILED DESCRIPTION OF THE INVENTION:

A first subject of the invention relates to a novel catalytic composition comprising at least one nickel complex, said complex being obtained from a mixture comprising:

at least one nickel precursor A, with
at least one imino-imidazole ligand B of formula (I)

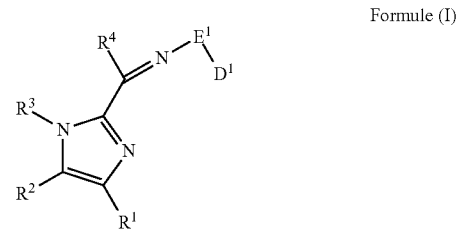

Formule (I)

in which $R^1$, $R^2$, $R^3$ and $R^4$ are identical or different and are chosen from the hydrogen atom, linear or branched alkyl groups, aryl, aralkyl or alkaryl groups comprising 1 to 12 carbon atoms and containing or not containing heteroelements, $R^1$ and $R^2$ not forming an aromatic ring; $E^1$ is a group chosen from the hydrocarbon groups: aliphatic, cyclic, aromatic, aromatic substituted with alkyl groups or containing or not containing heteroelements; $D^1$ is chosen from the hydrogen, nitrogen, sulphur, oxygen, or phosphorus atoms or from groups containing at least one nitrogen, sulphur, oxygen and/or phosphorus atom.

Preferably, $R^1$, $R^2$, $R^3$ and $R^4$ are chosen from the hydrogen, methyl, ethyl, isopropyl, isobutyl, tert-butyl, cyclohexyl, phenyl and benzyl groups; preferably, $R^1$, $R^2$ and $R^4$ are hydrogen atoms and, preferably, $R^3$ is a methyl group.

Preferably, $E^1$ is an aliphatic or aromatic group. Preferably, $E^1$ is chosen from the —$CH_2$—, —$CH_2CH_2$—, —$CH_2CH_2CH_2$—, —$CH_2CH_2CH_2CH_2$—, 1,2-phenylene, trans-1,2-cyclopentane, trans-1,2-cyclohexane, 2,3-butane, 1,1'-biphenyl, 1,1'-binaphthyl and —$Si(Me)_2$- groups. Very preferably, $E^1$ is the divalent —$CH_2CH_2$— group or the divalent 1,2-phenylene group.

Preferably, $D^1$ is chosen from a hydrogen atom, an ether of formula —$OR^5$, a thioether of formula —$SR^6$, an amine of formula —$N(R^7)_2$ or a phosphine of formula —$P(R^8)_2$ where $R^5$, $R^6$, $R^7$ and $R^8$ are hydrogen atoms, hydrocarbon groups: aliphatic, cyclic, aromatic, aromatic substituted with alkyl groups or containing or not containing heteroelements. Preferably, $R^5$, $R^6$, $R^7$ and $R^8$ are methyl, ethyl or phenyl groups.

The preparation of said imino-imidazole ligands B of formula (I) is carried out according to the methods known from the literature. For example, said ligands can be prepared according to the method of preparation described in the publications Org. Lett. 2007, 9, 18, 3699-3701 or Inorg. Chem. 2005, 44, 7431-7442.

The examples given in the present invention are only given for purposes of illustration and do not limit the present invention.

Said nickel precursor A used in the catalytic composition according to the invention is advantageously chosen from nickel(II) chloride, nickel(II) chloride (dimethoxyethane), nickel(II) bromide, nickel(II) bromide (dimethoxyethane), nickel(II) fluoride, nickel(II) iodide, nickel(II) sulphate, nickel(II) carbonate, nickel(II) dimethylglyoxime, nickel(II) hydroxide, nickel(II) hydroxyacetate, nickel(II) oxalate, nickel(II) carboxylates such as for example 2-ethylhexanoate, nickel phenates, nickel(II) acetate, nickel(II) trifluoroacetate, nickel(II) triflate, nickel(II) acetylacetonate, nickel (II) hexafluoroacetylacetonate, nickel bis(cycloocta-1,5-diene), nickel bis(cycloocta-1,3-diene), nickel bis(cyclooctatetraene), nickel bis(cycloocta-1,3,7-triene), bis (o-tolylphosphito)nickel(ethylene), nickel tetrakis (triphenylphosphite), nickel bis(ethylene), π-allylnickel(II) chloride, π-allylnickel(II) bromide, methallylnickel(II) chloride dimer, $\eta^3$-allylnickel(II) hexafluorophosphate, $\eta^3$-methallylnickel(II) hexafluorophosphate and nickel(II) 1,5-cyclooctadienyl, in their hydrated or unhydrated form, alone or in a mixture. Said nickel precursors can optionally be complexed with Lewis bases.

Said nickel precursors used in the catalytic composition according to the invention are advantageously prepared according to methods known from the literature. For example, said nickel precursors can be prepared according to the method of preparation described in patent applications WO 2004/083263 or WO 2001/74831 or in the publication *New J. Chem.* 2011, 35, 178-183.

The catalytic composition according to the invention can advantageously also contain a compound C, called an activating agent.

Said activating agent is advantageously chosen from the group formed by the tris(hydrocarbyl)aluminium compounds, chlorinated or brominated hydrocarbylaluminium compounds, aluminoxanes, organic compounds capable of acting as proton donors, organoboron compounds, alone or in a mixture.

The tris(hydrocarbyl)aluminium compounds and the chlorinated or brominated hydrocarbylaluminium compounds preferably correspond to the general formula $Al_xR''_yW_z$ in which R" represents a monovalent hydrocarbon radical containing for example up to 12 carbon atoms such as alkyl, aryl, aralkyl, alkaryl or cycloalkyl, W represents a halogen atom chosen for example from chlorine and bromine, W preferably being a chlorine atom, x takes a value from 1 to 2, y and z take a value from 1 to 3. As examples of such compounds, ethylaluminium sesquichloride ($Et_3Al_2Cl_3$), methylaluminium dichloride ($MeAlCl_2$), ethylaluminium dichloride ($EtAlCl_2$), isobutylaluminium dichloride ($iBuAlCl_2$), diethylaluminium chloride ($Et_2AlCl$), trimethylaluminium, tributylaluminium, tri-n-octylaluminium and triethylaluminium ($AlEt_3$) may be mentioned.

In the case where said activating agent is chosen from the aluminoxanes, said activating agent is advantageously chosen from methylaluminoxane (MAO), ethylaluminoxane and modified methylaluminoxane (MMAO). These activating agents can be used alone or in a mixture.

Preferably, said activating agent C is chosen from dichloroethylaluminium ($EtAlCl_2$) and methylaluminoxane (MAO).

In the case where said activating agent is chosen from organic compounds capable of acting as proton donors, said activating agent is preferably chosen from the acids of formula HX in which X represents an anion.

In the case where said activating agent is chosen from organoboron compounds, said activating agent is preferably chosen from Lewis acids of the tris(aryl)borane type such as tris(perfluorophenyl)borane, tris(3,5-bis(trifluoromethyl) phenyl)borane, tris(2,3,4,6-tetrafluorophenyl)borane, tris (perfluoronaphthyl)borane, tris(perfluorobiphenyl)borane and their derivatives and the (aryl)borates associated with a triphenylcarbenium cation or with a trisubstituted ammonium cation such as triphenylcarbenium tetrakis(perfluorophenyl)borate, N,N-dimethylanilinium tetrakis(perfluorophenyl)borate, N,N-diethylanilinium tetrakis(3,5-bis (trifluoromethyl)phenyl)borate, triphenylcarbenium tetrakis (3,5-bis(trifluoromethyl)phenyl)borate.

Another subject of the present invention relates to a method of oligomerization of olefins comprising from 2 to 10 carbon atoms using said catalytic composition. Preferably, said method is a method of oligomerization of ethylene, preferably a method of dimerization of ethylene.

Said nickel precursor A and said imino-imidazole ligand B of formula (I) can advantageously be mixed in order to obtain said nickel complex in the presence or absence of a solvent, called a preparation solvent. Said nickel complex of the catalytic composition according to the invention is advantageously prepared according to any method of preparation known to a person skilled in the art.

Said preparation solvent can advantageously be identical to or different from the reaction solvent, i.e. the solvent used for the method of oligomerization according to the invention and preferably for the method of dimerization. Said preparation and reaction solvents are advantageously chosen from organic solvents and preferably from the ethers, alcohols, chlorinated solvents and the saturated, unsaturated, aromatic or non-aromatic, cyclic or non-cyclic hydrocarbons. Preferably, said solvents are chosen from hexane, cyclohexane, heptane, butane or isobutane, monoolefins or diolefins preferably comprising 4 to 20 carbon atoms, benzene, toluene, ortho-xylene, mesitylene, ethylbenzene, dichloromethane, chlorobenzene, methanol, ethanol, pure or in a mixture, the mixture of olefins produced by said method of oligomerization and ionic liquids. In the case where said solvents are an ionic liquid, they are advantageously chosen from the ionic liquids described in patents U.S. Pat. No. 6,951,831 B2 and FR 2895406 B1.

Said nickel complex of the catalytic composition, diluted or not in said preparation solvent, can advantageously be used in the method of oligomerization according to the invention and preferably in the method of dimerization. An activating agent C can then optionally be added.

Said nickel complex of the catalytic composition can also advantageously be isolated and then used, diluted or not in a solvent, in the method of oligomerization according to the invention and preferably in the method of dimerization. An activating agent C can then optionally be added.

Said catalytic composition according to the invention can also advantageously be prepared in situ in the reaction section and in the solvent used for the method of oligomerization according to the invention and preferably for the method of dimerization. In this case, the order of mixing the nickel precursor A, the imino-imidazole ligand B of formula (I) and optionally the activating agent C is not critical.

Oligomerization is defined as the transformation of a monomer unit to a compound or mixture of compounds of general formula CpH2p with $4 \leq p \leq 80$, preferably with $4 \leq p \leq 50$, more preferably with $4 \leq p \leq 26$ and even more preferably with $4 \leq p \leq 14$.

The olefins used in the method of oligomerization according to the invention are olefins comprising from 2 to 10 carbon atoms and preferably said olefins are chosen from ethylene, propylene, n-butenes and n-pentenes, alone or in a mixture, pure or diluted. In the case where said olefins are diluted, said olefins are diluted with one or more alkane(s), such as those found in the "cuts" originating from petroleum refining processes, such as catalytic cracking or steam cracking.

Very preferably, the olefin used in the method of oligomerization according to the invention is ethylene.

Said olefins can come from non-fossil resources such as biomass. For example, the olefins used in the method of oligomerization according to the invention can advantageously be produced from alcohols, and in particular by dehydration of alcohols. In a preferred embodiment, said olefins are produced by dehydration of ethanol to produce ethylene.

The concentration of nickel in the catalytic solution is advantageously comprised between $1.10^{-5}$ and 1 mol/L, and preferably between $5.10^{-5}$ and $1.10^{-2}$ mol/L.

The molar ratio of the ligand B of formula (I) to the nickel precursor A is advantageously comprised between 0.05 and 10, preferably between 0.5 and 2 and more preferably 1.

The molar ratio of the activating agent C to the nickel complex is advantageously comprised between 1/1 and 1000/1, preferably between 100/1 and 1000/1 for the aluminoxanes and preferably between 1/1 and 20/1 for the other aluminium derivatives and the other Lewis acids.

The method of oligomerization according to the invention and preferably the method of dimerization of ethylene advantageously takes place at a total pressure comprised between atmospheric pressure and 20 MPa, preferably between 0.5 and 8 MPa, and at a temperature comprised between −40 and +250° C., preferably between −20° C. and 150° C.

The heat generated by the reaction can advantageously be removed by any of the means known to a person skilled in the art.

The method of oligomerization according to the invention and preferably the method of dimerization of ethylene can advantageously be carried out in a closed system, in a semi-open system or continuously, with one or more reaction steps. Vigorous stirring is advantageously utilized to ensure good contact between the reagent or reagents and the catalytic composition.

The method of oligomerization according to the invention and preferably the method of dimerization of ethylene can advantageously be implemented in batch mode. In this case, a chosen volume of the solution comprising the catalytic composition according to the invention is introduced into a reactor equipped with the usual devices for stirring, heating and cooling. The ethylene pressure and the temperature are adjusted to the desired values. The pressure inside the reactor is kept constant by introducing ethylene until the total volume of liquid produced represents, for example, 2 to 50 times the volume of the solution comprising the catalytic composition introduced originally. The catalytic composition is destroyed by any usual means known to a person skilled in the art, and then the products are withdrawn and separated from the solvent.

The method of oligomerization according to the invention and preferably the method of dimerization of ethylene can also advantageously be implemented continuously. In this case, the solution comprising the catalytic composition according to the invention is injected at the same time as the ethylene into a reactor stirred by standard mechanical means or by external recirculation, and maintained at the desired temperature. In another embodiment, the components of said catalytic composition can also be injected separately, for example the nickel precursor A and the ligand B on the one hand and the activating agent C on the other hand. The ethylene is introduced by a pressure-controlled admission valve, which keeps the pressure constant. The reaction mixture is withdrawn by means of a valve controlled by the liquid level so as to keep the latter constant. The catalytic composition is destroyed continuously by any usual means known to a person skilled in the art, then the reaction products as well as the solvent are separated, for example by distillation. Any unconverted olefin can be recycled to the reactor.

Said method according to the invention can advantageously be implemented in a reactor with one or more reaction steps in series, the olefin feedstock and/or the catalytic composition preconditioned beforehand being introduced continuously, either in the first step, or in the first and any other steps. At the reactor outlet, the catalytic composition can be deactivated, for example by injection of ammonia and/or of an aqueous solution of soda and/or an aqueous solution of sulphuric acid. The unconverted olefins and the alkanes optionally present in the feed are then separated from the oligomers by distillation.

The products of the present method can be used for example as components of motor fuels, as feedstock in a hydroformylation process for the synthesis of aldehydes and alcohols and/or as feedstock in a metathesis process for the synthesis of propylene for example.

The following examples illustrate the invention without limiting its scope.

EXAMPLES ACCORDING TO THE INVENTION

Example 1

Preparation of the Ligand L-1 (Compound B)

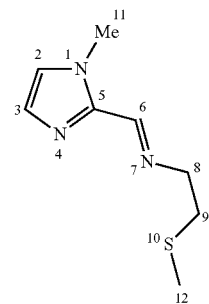

L-1

2-(Methylthio)ethylamine (440.1 mg; 4.89 mmol) is added to a solution of 1-methyl-2-imidazolecarboxyaldehyde (490 mg; 4.45 mmol) in 15 mL of dichloromethane. The yellow-coloured solution is stirred for 12 hours at ambient temperature. The solvent is then evaporated. The ligand L-1 is obtained in the form of a pale yellow oil with a yield of 90%. Characterization by $^1$H and $^{13}$C NMR and IR confirms the structure of the ligand L-1.

$^1$H NMR (300 MHz, $CD_2Cl_2$): δ=8.28 (dd, J=1.9, 1.3 Hz, 1H, $H_6$), 7.05 (d, J=1.0 Hz, 1H, $H_3$), 6.95 (s, 1H, $H_2$), 3.95 (s, 3H, $H_{11}$), 3.77 (td, J=6.8, 1.3 Hz, 2H, $H_8$), 2.79 (t, J=6.8 Hz, 2H, $H_8$), 2.12 (s, 3H, $H_{12}$).

$^{13}$C NMR (75 MHz, $CD_2Cl_2$): δ=154.57 (1C, $C_6$), 143.45 (1C, $C_5$), (129.36 (1C, $C_3$), 125.22 (1C, $C_2$), 61.33 (1C, $C_8$) 35.48 (2C, $C_9$, $C_{11}$), 15.83 (1C, $C_{12}$).

FT-IR: 2914w, 1648s, 1517w, 1476m, 1435s, 1366w, 1286m, 1228w, 1147w, 1044w, 919w, 793w, 756m, 707m, 689m.

Example 2

Preparation of the Complex Ni-1

A yellow solution of ligand L-1 (284 mg; 1.55 mmol) in 15 mL of dichloromethane is added dropwise to a suspension of nickel precursor (compound A) $NiCl_2$,dimethoxyethane in 10 mL of dichloromethane (325 mg; 1.48 mmol). The reaction medium turns green instantaneously. The suspension obtained is stirred for 12 hours at ambient temperature. The pale green precipitate formed is filtered via a cannula, washed cold with dichloromethane (3×20 mL), and then dried under vacuum. The complex Ni-1 is thus obtained. The yield from the reaction is 95%.

Example 3

Preparation of the Ligand L-2

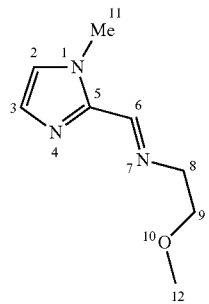

L-2

For synthesis of the ligand, the procedure in Example 1 is followed, except that the amine used is 2-(methoxy)ethylamine. The ligand L-2 is obtained in the form of a pale yellow oil with a yield of 92%. Characterization by $^1$H and $^{13}$C NMR and IR confirm the structure of the ligand L-2.

$^1$H NMR (300 MHz, $CD_2Cl_2$): δ=8.26 (s, 1H, $H_6$), 7.04 (s, 1H, $H_3$), 6.94 (s, 1H, $H_2$), 3.95 (s, 3H, $H_{11}$), 3.75-3.69 (m, 2H, 1-$1_9$), 3.66-3.69 (m, 2H, $H_8$), 3.33 (s, 3H, $H_{12}$).

$^{13}$C NMR (75 MHz, $CD_2Cl_2$): δ=154.96 ($C_6$), 143.59 ($C_s$), 129.32 ($C_3$), 125.12 ($C_2$), 72.53 ($C_9$), 61.64 ($C_8$), 58.86 ($C_{12}$), 35.46 ($C_{11}$).

FT-IR: 2875w, 1660s, 1516w, 1475 m, 1437s, 1366w, 1287 m, 1191w, 1118s, 1053w, 1026w, 955w, 919w, 832w, 802m, 757m, 708m, 690m.

Example 4

Preparation of the Complex Ni-2

For synthesis of the complex, the procedure in Example 2 is followed except that the ligand used for complexing the nickel is the ligand L-2. The complex Ni-2 is obtained in the form of a pale blue solid with a yield of 94%.

Example 5

Preparation of the Ligand L-3

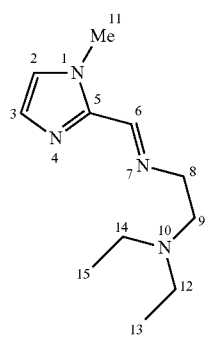

L-3

For synthesis of the ligand, the procedure in Example 1 is followed, except that the amine used is N,N-diethylethylenediamine. The ligand L-3 is obtained in the form of a yellow oil with a yield of 90%. Characterization by $^1$H and $^{13}$C NMR and IR confirms the structure of the ligand L-3.

$^1$H NMR (300 MHz, $CD_2Cl_2$): δ=8.25 (s, 1H, $H_6$), 7.03 (d, J=0.9 Hz, 1H, $H_3$), 6.93 (s, 1H, $H_2$), 3.95 (s, 3H, $H_{11}$), 3.63 (td, J=6.7, 1.3 Hz, 2H, $H_8$) 2.72 (t, J=6.8 Hz, 2H, $H_9$), 2.55 (q, J=7.1 Hz, 4H, $H_{12}$, $H_{14}$), 1.00 (t, J=7.1 Hz, 6H, $H_{13}$, $H_{15}$).

$^{13}$C NMR (75 MHz, $CD_2Cl_2$): δ=154.16 ($C_6$), 143.83 ($C_5$), 129.23 ($C_3$), 124.99 ($C_2$), 60.70 ($C_8$), 54.04 ($C_9$), 47.84 ($C_{12}$, $C_{14}$), 35.44 ($C_{11}$), 12.36 ($C_{13}$, $C_{15}$).

FT-IR: 2967w, 1650s, 1475 m, 1437s, 1369w, 1287m, 1203w, 1148s, 1068w, 919w, 749m, 708m, 691m, 629s, 531s.

Example 6

Preparation of the Complex Ni-3

For synthesis of the complex, the procedure in Example 2 is followed, except that the ligand used for complexing the nickel is the ligand L-3. The complex Ni-3 is obtained in the form of an orange solid with a yield of 89%.

Example 7

Preparation of the Ligand L-4

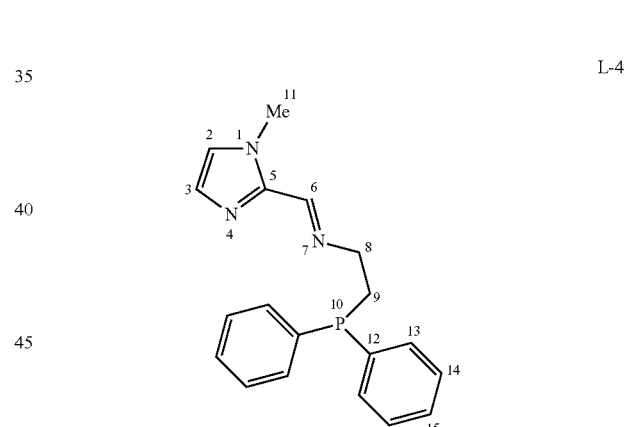

L-4

For synthesis of the ligand, the procedure in Example 1 is followed, except that the amine used is 2-(diphenylphosphino)ethylamine. The ligand L-4 is obtained in the form of a yellow oil with a yield of 95%. Characterization by 1H, $^{13}$C, $^{31}$P NMR and IR confirms the structure of the ligand L-4.

$^1$H NMR (300 MHz, $CD_2Cl_2$): δ=8.24 (s, 1H, $H_8$), 7.49-7.31 (m, 10H, $H_{14}$, $H_{15}$, $H_{16}$), 7.04 (d, J=1.0 Hz, 1H, $H_3$), 6.92 (s, 1H, $H_2$), 3.85 (s, 3H, $H_{11}$), 3.77-3.66 (m, 2H, $H_8$), 2.48-2.43 (m, 2H, $H_9$).

$^{31}$P NMR (121 MHz, $CD_2Cl_2$): δ=−19.09 (s, 1P, $P_{10}$).

$^{13}$C NMR (75 MHz, $CD_2Cl_2$): δ=153.95 ($C_6$), 143.55 ($C_5$), 139.23 ($C_{12}$), 133.23 ($C_{13}$), 129.35 ($C_3$), 128.86 ($C_{14}$), 128.77 ($C_{15}$), 58.95 ($C_8$), 35.47 ($C_{11}$), 30.22 ($C_9$).

FT-IR: 3051w, 1650s, 1518w, 1478m, 1434s, 1287w, 739m, 697m, 631m, 534s.

Example 8

Preparation of the Complex Ni-4

For synthesis of the complex, the procedure in Example 2 is followed, except that the ligand used for complexing the nickel is the ligand L-4. The complex Ni-4 is obtained in the form of an orange solid with a yield of 80%.

Example 9

Preparation of the Ligand L-5

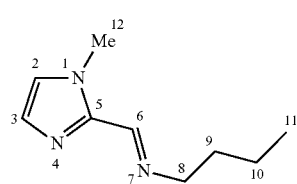

L-5

For synthesis of the ligand, the procedure in Example 1 is followed, except that the amine used is butylamine. The ligand L-5 is obtained in the form of a yellow oil with a yield of 95%. Characterization by $^1$H and $^{13}$C NMR and IR confirms the structure of the ligand L-5.

$^1$H NMR (300 MHz, CD$_2$Cl$_2$): δ=8.36 (d, J=6.2 Hz, 1H, H$_6$), 7.12 (s, 1H, 1¯1$_6$), 7.01 (s, 1H, H$_3$), 4.04 (s, 3H, H$_{12}$), 3.65 (td, J=6.8, 1.2 Hz, 2H, H$_8$), 1.73 (dq, J=12.2, 6.9 Hz, 2H, H$_9$), 1.58-1.41 (m, 2H, H$_{10}$), 1.03 (t, J=7.3 Hz, 3H, H$_{11}$).

$^{13}$C NMR (75 MHz, CD$_2$Cl$_2$): δ=153.31 (C$_6$), 143.77 (C$_5$), 129.11 (C$_3$), 124.92 (C$_2$), 61.93 (C$_8$), 35.41 (C$_{12}$), 33.52 (C$_9$), 20.76 (C$_{10}$), 14.00 (C$_{11}$).

FT-IR: 3107w, 2930m, 1650s, 1476m, 1437s, 1366w, 1287w, 1149w, 1026w, 919w, 859w, 748m, 628s, 528s.

Example 10

Preparation of the Complex Ni-5

For synthesis of the complex, the procedure in Example 2 is followed, except that the ligand used for complexing the nickel is the ligand L-5. The complex Ni-5 is obtained in the form of a light blue solid with a yield of 95%.

Example 11

Preparation of the Ligand L-6

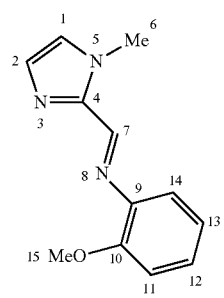

For synthesis of the ligand, the procedure in Example 1 is followed, except that the amine used is ortho-anisidine. The ligand L-6 is obtained in the form of an orange oil with a yield of 95%. Characterization by $^1$H and $^{13}$C NMR and IR confirms the structure of the ligand L-6.

$^1$H NMR (75 MHz, Acetone): δ 8.47 (s, 1H, H$_7$), 7.34-6.90 (m, 6H, H$_1$-H$_2$, H$_{11}$-H$_{14}$), 4.14 (s, 3H, H$_{15}$), 3.85 (s, 3H, H$_6$).

$^{13}$C NMR (75 MHz, Acetone): δ 153.29 (C$_7$), 144.39 (C$_{10}$), 142.02 (C$_4$), 130.52 (C$_2$), 127.64 (C$_{arom}$), 126.78 (C$_{arom}$), 124.64 (C$_1$), 121.86 (C$_{arom}$), 121.37 (C$_{arom}$), 113.07 (C$_{arom}$), 56.23 (C$_{15}$), 35.84 (C$_6$).

FT-IR: 2951w, 2835w, 1685w, 1626s, 1585m, 1514m, 1430s, 1366w, 1288m, 1243s, 1149w, 1115 m, 1048w, 1025 m, 965w, 869m, 745s, 631m, 536s.

Example 12

Preparation of the Complex Ni-6

For synthesis of the complex, the procedure in Example 2 is followed, except that the ligand used for complexing the nickel is the ligand L-6. The complex Ni-6 is obtained in the form of a light green solid with a yield of 95%.

Example 13

Oligomerization of Ethylene

The nickel complex (Ni-1-Ni-6) is dissolved in the reaction solvent and then is introduced into the reactor under an ethylene atmosphere. The activating agent is then added to the reactor. The reaction temperature is fixed at the test temperature, then the pressure is adjusted to the test pressure (see Table 1).

After a reaction time t, the introduction of ethylene is stopped. The reactor is cooled and degassed, then the products are analyzed by gas chromatography.

The mass of the products formed and the oligomer distribution are shown in Table 1.

TABLE 1

Oligomerization of ethylene by the complexes Ni-1 and Ni-6.[a]

| Entry | Complex | t (min) | m (g)[d] | Oligomer distribution[e] | |
|---|---|---|---|---|---|
| | | | | C$_4$ | C$_6$ |
| 1[a] | Ni-1 | 55 | 31.0 | 69 | 31 |
| 2[a] | Ni-2 | 60 | 9.3 | 78 | 22 |
| 3[a] | Ni-3 | 60 | 3.6 | 78 | 22 |
| 4[a] | Ni-4 | 60 | 17.6 | 82 | 17 |
| 5[a] | Ni-5 | 60 | 21.2 | 66 | 34 |
| 6[b] | Ni-1 | 52 | 30.1 | 71 | 29 |
| 7[b] | Ni-2 | 58 | 29.5 | 70 | 30 |
| 8[b] | Ni-3 | 58 | 29.7 | 71 | 29 |
| 10[b] | Ni-5 | 58 | 30.1 | 70 | 30 |
| 11[c] | Ni-1 | 20 | 66.8 | 84 | 16 |
| 12[c] | Ni-2 | 73 | 62.0 | 87 | 13 |
| 13[c] | Ni-6 | 20 | 64.5 | 87 | 13 |

[a]Heptane (25 mL), Ni (20 μmol), ethylene pressure 0.5 MPa, 45° C., activator: EtAlCl$_2$ (Al/Ni = 15).
[b]Toluene (25 mL), Ni (20 μmol), ethylene pressure 0.5 MPa, 45° C., activator: EtAlCl$_2$ (Al/Ni = 15).
[c]Heptane (100 mL), Ni (10 μmol), ethylene pressure 3 MPa, 45° C., activator: EtAlCl$_2$ (Al/Ni = 15).
[d]corresponds to the mass of oligomers produced during the test.
[e]wt. %, determined by GC.

The above examples demonstrate that the use of a novel catalytic composition according to the invention makes it possible to obtain very high selectivity for dimerization of ethylene.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application No. 11/02.731, filed 8 Sep. 2011, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A catalytic composition comprising at least one nickel complex, said complex being obtained from a mixture comprising:
   at least one nickel precursor A, with
   at least one imino-imidazole ligand B of formula (I)

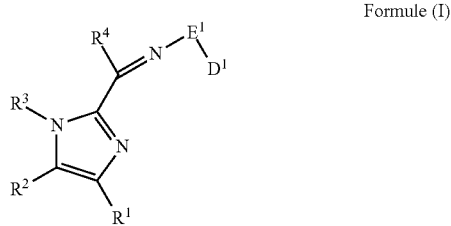

Formule (I)

in which $R^1$, $R^2$, $R^3$ and $R^4$ are identical or different and are hydrogen, linear or branched alkyl, aryl, aralkyl or alkaryl having up to 12 carbon atoms and optionally containing heteroelements, $R^1$ and $R^2$ not forming an aromatic ring; $E^1$ is —$CH_2$—, —$CH_2CH_2$—, —$CH_2CH_2CH_2$—, —$CH_2CH_2CH_2CH_2$—, 1,2-phenylene, trans-1,2-cyclopentane, trans-1,2-cyclohexane, 2,3-butane, 1,1'-biphenyl, 1,1'-binaphthyl or —$Si(Me)_2$—; $D^1$ is hydrogen, an ether of formula —$OR^5$, a thioether of formula —$SR^6$, an amine of formula —$N(R^7)_2$ or a phosphine of formula —$P(R^8)_2$ where $R^5$, $R^6$, $R^7$ and $R^8$ are methyl, ethyl or phenyl groups.

2. The catalytic composition according to claim 1 in which $R^1$, $R^2$, $R^3$ and $R^4$ are hydrogen, methyl, ethyl, isopropyl, isobutyl, tent-butyl, cyclohexyl, phenyl or benzyl.

3. The catalytic composition according to claim 1 in which $R^1$, $R^2$ and $R^4$ are hydrogen.

4. The catalytic composition according to claim 1 in which $R^3$ is methyl.

5. The catalytic composition according to claim 1 in which $E^1$ is divalent —$CH_2CH_2$-or divalent 1,2-phenylene.

6. The catalytic composition according to claim 1 in which said nickel precursor A used in the catalytic composition according to the invention is nickel(II) chloride, nickel(II) chloride (dimethoxyethane), nickel(II) bromide, nickel(II) bromide (dimethoxyethane), nickel(II) fluoride, nickel(II) iodide, nickel(II) sulphate, nickel(II) carbonate, nickel(II) dimethylglyoxime, nickel(II) hydroxide, nickel(II) hydroxyacetate, nickel(II) oxalate, a nickel(II) carboxylate, a nickel phenate, nickel(II) acetate, nickel(II) trifluoroacetate, nickel(II) triflate, nickel(II) acetylacetonate, nickel(II) hexafluoroacetylacetonate, nickel bis(cycloocta-1,5-diene), nickel bis(cycloocta-1,3-diene), nickel bis(cyclooctatetraene), nickel bis(cycloocta-1,3,7-triene), bis(o-tolylphosphito)nickel(ethylene), nickel tetrakis(triphenylphosphite), nickel bis(ethylene), π-allylnickel(II) chloride, π-allylnickel(II) bromide, methallylnickel(II) chloride dimer, $\eta^3$-allylnickel(II) hexafluorophosphate, $\eta^3$-methallylnickel(II) hexafluorophosphate or nickel(II) 1,5-cyclooctadienyl, in hydrated or unhydrated form, alone or in a mixture, optionally complexed with a Lewis base.

7. The catalytic composition according to claim 1 in which the catalytic composition contains a compound C activating agent, that is a tris(hydrocarbyl)aluminium compound, a chlorinated or brominated hydrocarbylaluminium compound, an aluminoxane, an organic compound capable of acting as a proton donor, or an organoboron compound, alone or in a mixture.

8. The catalytic composition according to claim 1 in which said nickel complex of the catalytic composition is prepared in the presence of a solvent.

9. A method of oligomerization of olefins having from 2 to 10 carbon atoms, comprising subjecting said olefins to oligomerization conditions in the presence of a catalytic composition according to claim 1.

10. The method according to claim 9 in which the olefins are ethylene, propylene, an n-butene or an n-pentene, alone or in a mixture, pure or diluted.

11. The method according to claim 9 in which said method is a method of oligomerization of ethylene.

12. The method according to claim 11 in which said method is a method of dimerization of ethylene.

13. The catalytic composition according to claim 6, wherein said nickel precursor A is 2-ethylhexanoate.

14. The catalytic composition according to claim 1 in which said nickel complex of the catalytic composition is prepared in the absence of a solvent.

* * * * *